United States Patent
Schleipen et al.

(10) Patent No.: US 9,075,052 B2
(45) Date of Patent: Jul. 7, 2015

(54) BIOSENSOR SYSTEM FOR SINGLE PARTICLE DETECTION

(75) Inventors: Johannes Joseph Hubertina Barbara Schleipen, Eindhoven (NL); Joannes Baptist Adrianus Dionisius Van Zon, Waalre (NL); Derk Jan Wilfred Klunder, Geldrop (NL); Toon Hendrik Evers, Eindhoven (NL); Josephus Arnoldus Henricus Maria Kahlman, Tilburg (NL); Ron Martinus Laurentius Van Lieshout, Geldrop (NL); Mikhail Mikhaylovich Ovsyanko, Eindhoven (NL)

(73) Assignee: Koninklijke Philips N.V., Eindhoven (NL)

(*) Notice: Subject to any disclaimer, the term of this patent is extended or adjusted under 35 U.S.C. 154(b) by 240 days.

(21) Appl. No.: 13/498,482

(22) PCT Filed: Sep. 23, 2010

(86) PCT No.: PCT/IB2010/054292
§ 371 (c)(1),
(2), (4) Date: Jun. 19, 2012

(87) PCT Pub. No.: WO2011/036634
PCT Pub. Date: Mar. 31, 2011

(65) Prior Publication Data
US 2012/0250005 A1    Oct. 4, 2012

(30) Foreign Application Priority Data
Sep. 28, 2009  (EP) .................................... 09171495

(51) Int. Cl.
G01N 21/00 (2006.01)
G01N 33/543 (2006.01)
(Continued)

(52) U.S. Cl.
CPC .......... G01N 33/54373 (2013.01); G01N 21/47 (2013.01); G01N 21/552 (2013.01);
(Continued)

(58) Field of Classification Search
USPC ......................................................... 356/338
See application file for complete search history.

(56) References Cited

U.S. PATENT DOCUMENTS 5,796,487 A    8/1998  Guerra
6,280,960 B1 *  8/2001  Carr ................................ 435/7.2
(Continued)

FOREIGN PATENT DOCUMENTS

JP          11211990 A    8/1999
NL  PCT/IB2009/053168    *  7/2009  ........... G01N 33/543
(Continued)

OTHER PUBLICATIONS

Sera-Mag Speedbeads, Magnetic Microparticles, Oct. 2006.
(Continued)

Primary Examiner — Tarifur Chowdhury
Assistant Examiner — Omar Nixon

(57) ABSTRACT

A biosensor system for the detection of particles includes a biosensor cartridge having a sensor surface. A biosensor magnet assembly is disposed on one side of the cartridge for generating a magnetic field effective at the cartridge and the sensor surface. The biosensor magnet assembly includes at least two magnetic sub-units separated by a gap. A first optical detection system detects the particles arranged at the same side of the cartridge as the magnet assembly. The magnet assembly and the first optical sensor are disposed such that the optical detection is accomplished through the gap of the magnet assembly.

9 Claims, 2 Drawing Sheets

(51) Int. Cl.
  *G01N 21/47* (2006.01)
  *G01N 21/552* (2014.01)
  *G01N 21/64* (2006.01)
  *G01R 33/12* (2006.01)
  *G01N 21/51* (2006.01)
  *G01N 21/49* (2006.01)
  *G01N 27/72* (2006.01)
  *G01N 15/10* (2006.01)
  *G01N 15/00* (2006.01)

(52) U.S. Cl.
  CPC ........ *G01N21/6458* (2013.01); *G01R 33/1269* (2013.01); *G01N 21/51* (2013.01); *G01N 15/10* (2013.01); *G01N 15/1031* (2013.01); *G01N 21/49* (2013.01); *G01N 27/72* (2013.01); *G01N 33/54313* (2013.01); *G01N 2015/0065* (2013.01); *G01N 2201/12* (2013.01)

(56) References Cited

U.S. PATENT DOCUMENTS

| | | | |
|---|---|---|---|
| 7,315,374 B2* | 1/2008 | Tan et al. | 356/399 |
| 2002/0093654 A1 | 7/2002 | Lieberman | |
| 2003/0205681 A1 | 11/2003 | Modlin | |
| 2004/0197267 A1* | 10/2004 | Black et al. | 424/9.6 |
| 2005/0186565 A1* | 8/2005 | Malak | 435/5 |
| 2006/0050268 A1* | 3/2006 | Talley et al. | 356/301 |
| 2007/0178607 A1* | 8/2007 | Prober et al. | 436/522 |
| 2008/0252884 A1 | 10/2008 | Carr | |
| 2009/0053700 A1 | 2/2009 | Griffiths | |
| 2009/0170212 A1* | 7/2009 | Van Der Wijk et al. | 436/149 |

FOREIGN PATENT DOCUMENTS

| | | |
|---|---|---|
| WO | 2007050743 A2 | 5/2007 |
| WO | 2008017972 A2 | 2/2008 |
| WO | 2008107827 A1 | 9/2008 |
| WO | 2008139356 A1 | 11/2008 |
| WO | 2009007797 A1 | 1/2009 |
| WO | 2009007888 A1 | 1/2009 |
| WO | 2009040746 A1 | 4/2009 |
| WO | 2010044006 A2 | 4/2010 |

OTHER PUBLICATIONS

Jin, L. et al "Application of Total Internal Reflection Fluorescence (TIRF) Microscopy in Cellular Bio-Imaging" The Chinese University of Hong Kong, Department of Biochemistry, IEEE Explore, 2010, pp. 587-589.

Atlan, Michael et al "Heterodyne Holographic Microscopy of Gold Particles" Physics. Optics, Feb. 2008.

* cited by examiner

BIOSENSOR SYSTEM FOR SINGLE PARTICLE DETECTION

FIELD OF THE INVENTION

The present invention relates to a biosensor system.

BACKGROUND OF THE INVENTION

Various analytical procedures to detect an analyte in a test sample or sample volume are known in the prior art.

For example, immunoassays use the mechanisms of the immune system, wherein antibodies and the respective antigens are capable of binding to each other. This specific reaction mechanism is used to determine the presence or quantity of the antigen in a test sample. In particular, the antibody or the antigen (analyte of interest) is labeled to quantify the interactions between antibody and antigen. Common labels are, for example, fluorescent and chemiluminescent molecules, colored particles (beads) or radioisotopes. In general all these are referred to here as particles. A certain application is the optical detection of magnetic particles bound to the antigen to be detected in various manners. Thereby, by detecting the magnetic particles, the amount of antigen or analyte can be concluded.

Recently, magnetic labels have been used in microfluidic assays to detect the presence or quantity of an analyte. The use of magnetic labels as, for example, magnetic particles, also denominated as magnetic beads or beads, has several advantages. The magnetic particles can be actuated by applying a magnetic field such that the analytical procedure can be accelerated. Further, there is no magnetic background signal in the biological test sample influencing the detection of the magnetic particles.

The performance of known systems in the sub-pM regime is limited by optical baseline drift and non-specifically bound beads. A non-specifically bound bead normally is not wanted for detection, it is an aim to receive a detection signal based only on bound beads or particles. Thus, increasing the optical resolution would be beneficial in terms of higher stability and detailed information on single particles or beads.

High numerical apertures, required for single bead identification will result in a high degree of optical aberrations, limiting the resolution of the imaging optics of known systems to several microns.

A recently known magnetic bio sensor system makes use of Frustrated Total Internal Reflection (FTIR) to detect the presence of magnetic beads near a surface of an assay. The signal is more or less linearly dependent on the concentration of beads on the surface (the surface density ñ). The signal (i.e. the decrease of the totally internal reflected signal) can be expressed as:

$$S = \beta \cdot \tilde{n}$$

where S is the measured signal change in % and $\beta$ is a conversion factor from surface density to signal change. The limit of detection of this technique is mainly determined by drift in the background signal which contributes to about 0.1% of signal change. This is equivalent to a surface density of 1 bead per 200 um$^2$ which can be detected with this FTIR platform.

For a channel height of 480 μm, the minimum detectable target concentration would be about 20 fM. However, in practice the assay efficiency is an order of magnitude lower, bringing the detection limit to 200 fM. Besides the drift in the background signal, also the signal of nonspecifically bound beads limits the minimum detectable concentration. These beads are bound to the surface via a non-specific bond, e.g. an antibody-antibody bond instead of a specific bond like antibody-target-antibody.

SUMMARY OF THE INVENTION

It is an object of the invention to provide a biosensor system capable for detecting single particles.

Provided is a biosensor system for the detection of particles comprising:
  a biosensor cartridge comprising a sensor surface,
  a biosensor magnet assembly on one side of the cartridge for generating a magnetic field effective at the cartridge and the sensor surface, the first biosensor magnet assembly comprising at least two magnetic subunits separated by a gap,
  a first optical detection system for detecting the particles arranged
  at the same side of the cartridge as the magnet assembly, whereas the magnet assembly is designed in a way that the optical detection is accomplished through the gap of the magnet assembly.

Further provided is a method for the detection of particles with a corresponding biosensor system.

Further provided is a use of a corresponding biosensor system in one or more of the following applications:
  biosensors used for molecular diagnostics
    rapid and sensitive detection of proteins and nucleic acids in complex biological mixtures such as e.g. blood or saliva
    high throughput screening devices for chemistry, pharmaceuticals or molecular biology
    testing devices e.g. for DNA or proteins e.g. in criminology, for on-site testing (in a hospital), for diagnostics in centralized laboratories or in scientific research
    tools for DNA or protein diagnostics for cardiology, infectious disease
    and oncology, food, and environmental diagnostics
    tools for combinatorial chemistry
    analysis devices
    nano- and micro-fluidic devices
    drug release and drug delivery systems (in particular transdermal and implantable drug delivery devices).

The bio sensor system described is capable of detecting single particles and actuating the particles simultaneously by a magnetic field. A compact and space-saving biosensor system is presented, also applicable for portable applications.

Non restrictive examples of the invention are described in the following dependent claims.

One example is a biosensor system comprising a second optical detection system for detecting the particles, providing the light for the first optical detection system by scattering of light at the particles. The information of the second optical detection system about the particles can be used additionally. Signals of the first and second optical detection system can be compared and combined In this case the first and the second optical detection system can be combined in a way that an incoming ray of the second optical detection system is used as light source of the first optical detection system, saving an additional light source.

Another example discloses a biosensor system, whereby the magnet assembly and the first optical detection system are designed in a way that a light cone of an incoming ray generated by scattering at the particles for detecting the particles projects through end sections of the at least two magnet subunits of the magnet assembly allowing the actuation of particles by the magnet assembly and the detection of the particles at the sensor surface at the same time. The biosensor system according to this example permits the magnet assembly to be positioned in a compact way not to interfere with the first optical detection system. A magnetic actuation of the magnetic particles is accomplished without restricting the optical detection. The space at the top side of the cartridge contrary to the first optical detection system and the magnet assembly is saved.

Another example discloses a biosensor system, whereby the magnet assembly with the at least two magnetic subunits is arranged essentially at a perpendicular direction regarding the first optical detection system, and the end sections of the at least two subunits projecting essentially upwards in the same direction as the first optical detection system perpendicular to the at least two subunits. These features enable a proper magnetic actuation at the sensor surface. The magnetic field of the magnet assembly is designed in a way that magnetic field lines project essentially parallel to the sensor surface in the area of the sensor surface. The magnetic field generated by the magnet assembly with the end sections described allows an effective magnetic actuation along the sensor surface.

Another example discloses a biosensor system, whereby the second optical detection system is based on TIR (Total Internal Reflection) or on FTIR (Frustrated Total Internal Reflection) detection and the second optical detection system comprises a microscope based on Dark Field Microscopy (DFM) designed to resolve single particles and a camera designed to image single particles resolved by the microscope. A combined biosensor system is established with a compact structure, a high resolution, and an automatic read out of the microscope by the camera.

Another example discloses a biosensor system, comprising a processor receiving signals from the first optical detection system and the second optical detection system, whereby both signals are processed to a resulting signal characterizing the presence or location of at least one single particles. Not only the amount of particles but also the location of the detected particles are determined, especially the location of the particles with regard to the sensor surface. The signals by the first and second optical detection system are compared and/or combined in the processor.

A further example discloses a biosensor system, whereby signals from the second optical detection system resulting from improper particles are subtracted from the signals from the first optical detection system leading to a signal resulting only from proper particles. The term proper signal denotes especially signals originating from correctly or specifically bound particles. Improper bindings are bindings in which the wrong particles bind to each other and these therefore harm the measurement.

A further example discloses a biosensor system, whereby an entrance angle α between an incoming ray and an outgoing ray of the first optical detection system lies in a range between 65° and 75°, the cartridge thickness d lies in a range between 0.3 mm and 2 mm, the width $w_{opt}$ of a sensor area of the sensor surface is about 1 mm, the numerical aperture (NA) of the lens has a minimum value satisfying the equation $$NA_{min} = \frac{\frac{1}{2}\lambda}{d_{bead}},$$

the width of a pole tip of the magnetic subunit is about 0.25 mm, and the air gap between pole tips of the magnetic subunit is smaller than 1.5 mm.

BRIEF DESCRIPTION OF THE DRAWINGS

These and other aspects of the invention will be apparent from and elucidated with reference to the embodiments described hereinafter.

In the drawings.

DETAILED DESCRIPTION OF EMBODIMENTS

Figure 1:
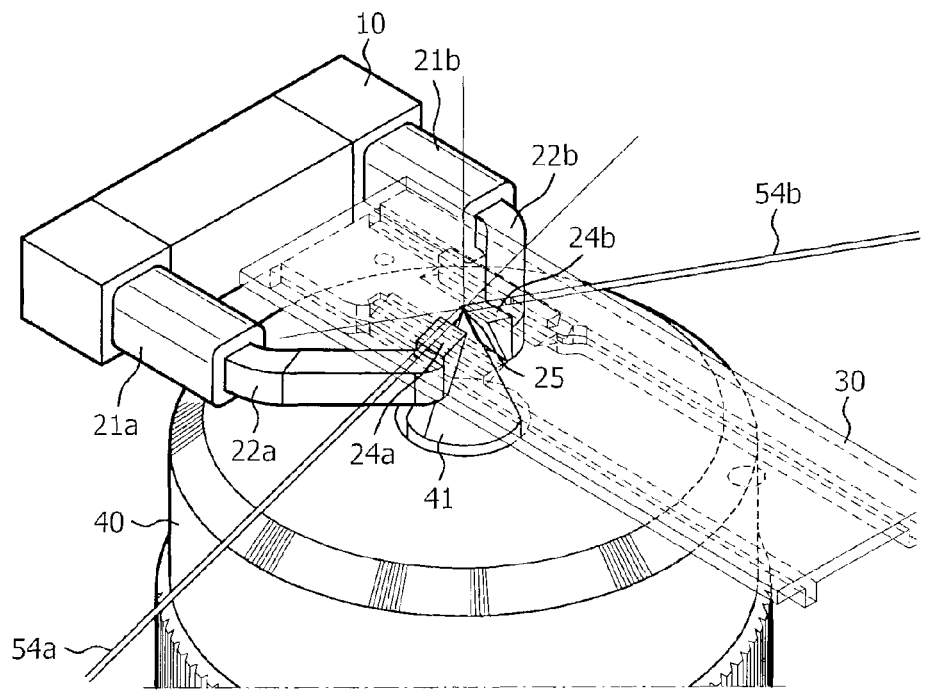
FIG. 1 shows a perspective view of an example of the biosensor system with a lens of a microscope below, above the lens of the microscope two magnetic subunits of a magnet assembly with end sections, and a cartridge with a sensor surface positioned above the end sections, further shown is an incoming and outgoing ray light directed to an optical detection unit.

FIG. 1 shows a perspective view of an example of the biosensor system 1 with a microscope 42 as part of a first optical detection system 40 below, above the microscope 42 in this example two magnetic subunits 22a, 22b of a magnet assembly 10 with end sections 24a, 24b are shown. Shown is a cartridge 30 with a sensor surface 31 positioned above the end sections 24a, 24b in this view. In this example the two subunits 22a, 22b are positioned perpendicular to the longitudinal direction of the microscope 42. The end sections 24a, 24b of the corresponding magnetic subunits 22a, 22b project in an essentially perpendicular direction to the magnetic subunits 22a, 22b, this is the direction essentially parallel to the longitudinal axis of the microscope 42, in the shown perspective upwards. The cartridge 30 is positioned above the magnetic subunits 22a, 22b and corresponding end sections 24a, 24b. The magnet assembly 10 generates a magnetic field that exerts magnetic forces in the area of the sensor surface 31 of the cartridge 30 to accomplish a magnetic actuation. The magnetic field exerts forces especially at magnetic particles 2 within the cartridge 30 and enables the magnetic actuation process, the binding of the magnetic particles 2 with other particles 2 to be analyzed. The actuation process is well known in the state of the art. A lens 43 below the microscope 42, the microscope 42, and a camera 44 below the lens 43 are parts of the first optical detection system 40 described below. An incoming ray 54a of a light source, for instance an LED or laser (not shown) coming from the left side impinges at the sensor surface 31. Particles 2 present at the sensor surface 31, especially magnetic particles 2, scatter parts of the incoming ray 54a, the scattered light 46 is used for the detection of the particles 2 by the first optical detection system 40. It is to be understood that only this scattered light 46 is used for the detection of the particles 2 by the first optical detection system 40. Scattered light 46 in FIG. 1 is depicted as a light cone 41 starting from the sensor surface 31 and spreading in the direction of a lens 43 of the first optical detection system 40. An outgoing ray 54b leaves the cartridge 30 originating from the incoming ray 54a after impinging at the sensor surface 31 and being scattered. The biosensor system 1 shown is usually integrated into a housing 51b and may be applied in a portable handheld device (not shown). In a further example the outgoing ray 54b can also be used for a further detection of the particles 2 by the second optical detection system. Magnetic beads or particles 2 with a diameter of 500 nm are visible by means of the microscope 42 with sufficient magnification and resolution. In this case the surface density of the particles 2 can be determined by counting the number of individual beads or particles 2 within the field of view at the sensor surface 31. E.g. when the field of view has an area of 1 mm$^2$, the lowest measurable surface density would be 1 bead per 1 mm$^2$ or 1 bead per 106 µm$^2$. With regard to a known minimal detectable surface density of 1 bead per 200 µm$^2$, such a counting method results in an increase in sensitivity of a factor 5000. This brings the minimum detectable target concentration of an analyte to be measured within the region of interest, e.g. 1 fM. Single bead detection offers an enhancement of the sensitivity by at least 2 to 3 orders of magnitude. Because beads or particles 2 are detected discrete, counting single particles 2, leading to a digital detection, the method and biosensor system 1 is insensitive to drift.

In a common microscope, where front side or backside illumination sources are used, no or little accurate information is obtained about the height of the bead or particles 2 above the sensor surface 31. In the setup described here height information, in which distance the particle 2 is located to the sensor surface 31, is present in the signal, because the beads or particles 2 are located in a more or less exponential decaying evanescent field. The decay length of the evanescent field is in the order of 50 nm to 150 nm. Changes in the height position in the order of a few nanometer are therefore detectable by this biosensor system 1. Height and/or height changes can provide valuable information about the binding state of the bead or particle 2.

Figure 2:
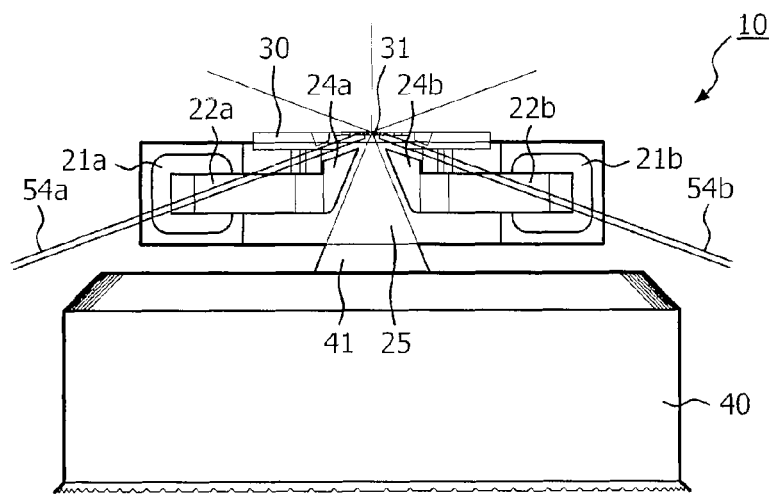
FIG. 2 shows a similar example as FIG. 1 in a side view.

FIG. 2 shows a similar example as FIG. 1 in a side view. The view of FIG. 2 makes clear the combination of the magnet assembly 10 for providing a magnetic field at the cartridge 30 and the optical detection of particles 2 by the first optical detection system 40. Again, the incoming ray 54a is reflected at the sensor surface 31 of the cartridge 30, a small part of the incoming ray 54a is reflected at the particles 2 and serves as a light source for the first optical detection system 40. The reflected light is again depicted as a cone 41 in a schematic way. Especially, the end sections 24a, 24b of the magnetic subunits (22a, 22b) are directed vertical, whereas the magnetic subunits (22a, 22b) are aligned horizontal. The end sections 24a, 24b are directed upwards essentially in a right angle to the magnetic subunits 22a, 22b, and essentially parallel to the longitudinal axis of the microscope 42, this is the longitudinal direction of the plane of FIG. 2. The structure described allows for the magnet assembly 10 and the first optical detection system 40 to be positioned at the same side with regard to the cartridge 30. Solving the problem of aligning all necessary parameters is described below. The magnetic subunits 22a, 22b define a gap 25 between each other. Adjacent to the gap 25 and above the gap 25 in this view some of the light of the incoming light ray 54a is scattered to the direction of the first optical detection system 40. The gap 25 is formed in a way to house the scattered light 46 depicted by the light cone 41, the light cone 41 fits into the gap 25, as is shown in FIG. 2. The described structure allows for the first optical detection system 40 and the magnet assembly 10 for magnetic actuation to be positioned at the same side of the cartridge 30. The present biosensor system 1 is adapted to actuate particles 2 and detect particles 2 simultaneously. This biosensor system 1 described opens the possibility for bond length and bond strength analysis on an individual particle or bead basis allowing the discrimination between specifically and nonspecifically bound beads or particles 2. Nonspecifically bound particles 2 are unwished and contribute to false signal results. The aim is to measure only specifically bound particles 2, e.g. magnetic particles 2, bound to analyte which is to be measured. Discrimination between specifically and nonspecifically bound particles 2 can lower the detection limit by reducing the contribution of nonspecifically bound particles 2. Hence, complete physical elimination of the non-specific binding of particles 2 is not necessary anymore. This relaxes demands put on the performance of the biosensor system 1.

Figure 3:
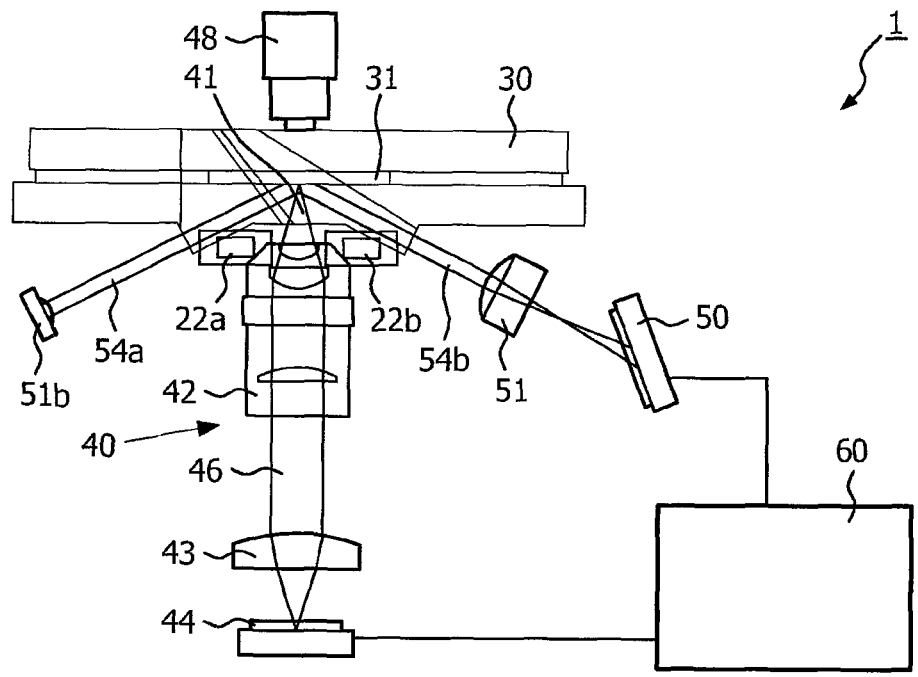
FIG. 3 shows a schematic side view of a bio sensor system according to an example of the invention with a first optical detection system in the centre and a second optical detection system at the left and right side, above two magnetic subunits, above a cartridge with sensor surface, and an additional magnetic unit at the top.

FIG. 3 shows a schematic side view of a bio sensor system according to an example of the invention with a first optical detection system 40 in the centre and a second optical detection system 50 at the right side. The second optical detection system 50 is based on the principle of TIR (Total Internal Reflection) or FTIR (Frustrated Total Internal Reflection) in this example.

For completeness, in the following examples of optical methods are disclosed, e.g. a dark field detection with a spatial filtering (not shown) in the second optical detection system 50 that is additionally arranged in the path of the outgoing light ray 54b between the cartridge 30 and the second optical detection system 50. A clear advantage of the FTIR detection method is the use of well-collimated parallel incoming light ray 54a illuminating the sensor surface 31, and hitting the second optical detection system 50 after reflection. When using an imaging (convergent) lens 51 in the second optical detection system 50 of the detection branch, virtually all the totally internally reflected light of the outgoing light ray 54b is going through the focal plane of the lens 51 and (depending on the NA (Numerical Aperture) of the lens 51 and the wavelength of the light) is concentrated in a very small area in the focal plane (Fourier plane) of the imaging lens 51. In one example, the light further propagates towards the image plane hitting the second optical detection system 50 and generating there a bright-field image of the sensor surface 31. According to a different example, a spatial filter (obstruction mask, not shown) is however positioned in the Fourier plane of the imaging lens 51 with a dimension slightly larger than the focused spot. This has the effect that all light stemming from total internal reflection will be blocked by the obstruction and none of this light is hitting the detector 50, resulting in a zero optical signal (i.e. dark image) when no scattering takes place at the sensor surface 31, referred to as dark field detection. It is to be said that alternatively to scattered light as described above fluorescent photons can be used for dark field detection. The first optical detection system 40 can be designed with a camera 44 having a low NA. Providing a camera 44 with a high NA nevertheless enables the system 1 to identify single particles 2. Alternatively, the first optical detection system 40 may for detection with lower requirements comprise a Si pin-diode, or a 1D- or 2D array of pin-diodes instead of the camera 44. The latter is applicable for multiplexing of assays to be detected.

When a binding of target particles 2 takes place at the sensor surface 31, scattering of light results in light being scattered in random directions, other than the direction of the main reflected outgoing light ray 54b. Consequently, these scattered rays will pass the Fourier plane of the lens 51 off-axis, and will not be blocked by the on-axis obstruction of a filter for dark field imaging, resulting in some light on the second optical detection system 50. Since the scattered light is still imaged onto the second optical detection system 50, the measured signal is now directly proportional to the amount of scattering, which is proportional to the amount of bound target particles 2. In this way one obtains an optical 'x-signal', which can be processed by the processor 60 with a high SNR.

A light source 51b is positioned at the left side of the first optical detection system 40 for generating the incoming light ray 54a impinging at the sensor surface 31 of the cartridge 30. A part of the light of the incoming ray 54a is scattered in the direction downwards between the magnetic subunits 22a, 22b. The rest of the incoming light ray 54a is directed to the second optical detection system 50, passing a lens 51 before detection. The scattered light 46 passes a lens 43 and reaches the camera 44 at the bottom of the first optical detection system 40 for automatic detection of the image of the microscope 42 and recording. The first optical detection system 40 and the second optical detection system 50 are connected to a processor 60 for processing the feeded signals regarding the particles 2. A further magnet unit 48 is provided above the cartridge 30 for generating a further magnetic field to support the magnetic actuation process or for removing excessive particles 2 by magnetic forces, a method known as magnetic washing. The top side of the cartridge 30 remains fully accessible, allowing the positioning of the further magnet unit 48 for magnetic washing, a heater for temperature control or other devices.

Figure 4:
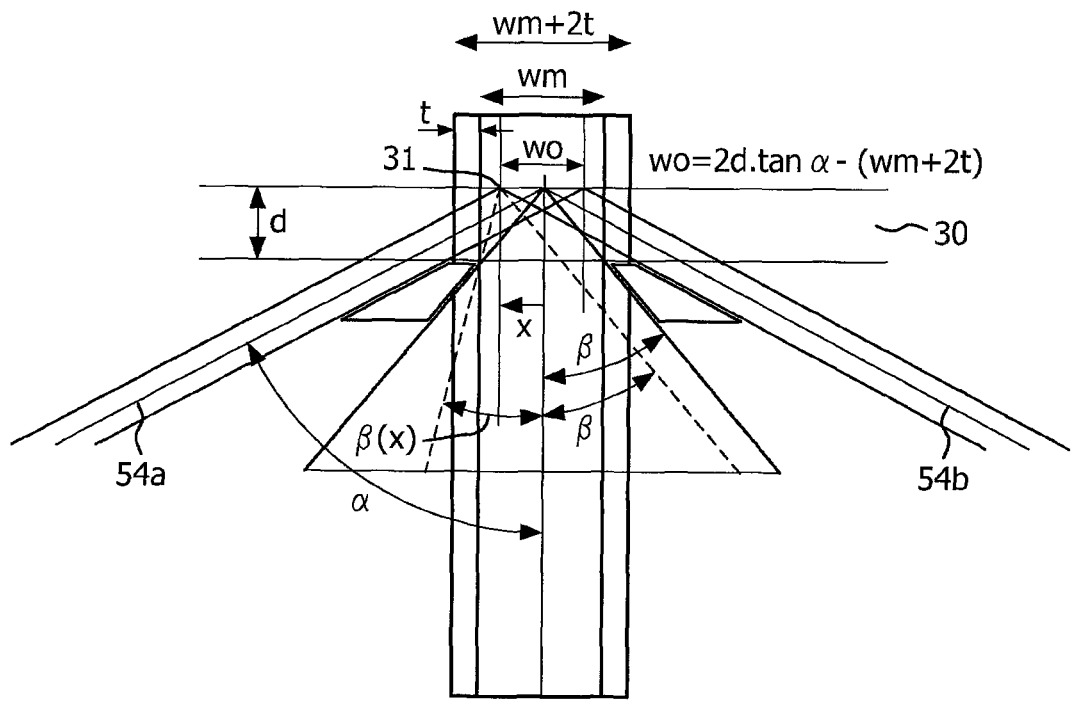
FIG. 4 shows a side view of a cartridge with several indications of sizes and angles of light beams impinging at the cartridge.

FIG. 4 shows a side view of the cartridge 30 with several indications of sizes and angles of light beams, incoming ray 54a, outgoing ray 54b, impinging at the cartridge 30. The described sizes of the parameters are preferred. In the example shown under FIG. 3 the second optical detection system 50 is based on FTIR illumination comprising a LED or a laser light source as light source 51b, and some known collimation optics for collimating the output of the light source 51b. In order to fulfill the conditions for total internal reflection (TIR) and to create an evanescent field in the sample volume of the cartridge 30 comprising the analyte just above the cartridge 30, the angle of the incoming light beam or ray 54a should exceed the critical angle .theta. for total internal reflection, which is given by the formula $\theta = \sin^{-1}(n_{sample}/n_{cartridge})$ where n is the index of refraction. For a plastic-water like optical interface ($n_{sample}=1.3$, $n_{cartridge}=1.5$) the critical angle is in the order of 58 degrees. In order to cope with finite divergence of the light beam and to have sufficient system margin the entrance angle in the platform of FIG. 3 is fixed at 70 degrees. It is worthwhile to mention here that the decay length θ of the evanescent field depends on the entrance angle of the incoming ray 53a, according to the following formula, where θ is the wavelength of the light, $n_{cartridge}$ and $n_{sample}$ are the refractive indices of the cartridge 30 and sample fluid respectively:

$$\zeta(\lambda, \theta, n_{cartridge}, n_{sample}) = \frac{\lambda}{2\pi\sqrt{n_{cartridge}^2 \sin^2(\theta) - n_{sample}^2}}$$

For the example of the FTIR detection optics of the second optical detection system 50 an imaging lens is required, positioned at some distance from the cartridge 30, imaging the cartridge surface, the sensor surface 31, onto the CMOS or CCD camera 44. Note that the camera 44 is positioned under an angle with respect to the optical axis of the scattered light 46, in order to compensate for tilt/defocus introduced by the slanted orientation of the sensor surface 31 of the cartridge 30 with respect to the optical axis (also known as Scheimpflug condition). The combination of focal length of the imaging lens 43 and distance from cartridge 30 to camera 44 determines the optical magnification from cartridge 30 to camera 44. In the second optical detection system 50 shown under FIG. 3 an imaging lens 43 is being used having a focal length in the range of 15 mm with an effective numerical aperture well below 0.1. As a result the optical resolution of the second optical detection system 50 in is the order of 10 to 15 microns and single beads or particles 2 of the size described cannot be resolved in the contrary to the first optical detection system 40.

An important requirement for the magnet assembly 10 is the distance between the poles, henceforth called the air gap or gap 25. The gap 25 largely determines the shape of the fringing field of the magnet assembly 10 and thus the magnetic force which can be generated. A reasonable magnetic force (several 100 fN) is required to attract the magnetic beads or particles 2 from the liquid into the cartridge 30, in which the analyte is dissolved, towards the sensor surface 31 to enhance the concentration of beads with the analyte and increase the binding kinetics. Smaller air gaps provide larger forces. When the gap 25 becomes wider, first of all the magnetic force becomes less but also the profile of the force distribution changes. A small gap 25 provides a magnetic force profile where the magnetic force is mainly concentrated at the center between the end sections 24a, 24b of the magnet subunits 22a, 22b, which is basically the area of interest to do the measurement. For wider gaps 25 the force profile changes from one concentrated location at the center of the end sections 24a, 24b to two concentrated locations near the position of the poletips of the end sections 24a, 24b. Basically the two magnet subunits 22a, 22b start behaving more and more like two separate magnets. This is not a desired situation because these spots are outside the area of interest. Because of this requirement the size of the gap 25 is limited to a maximum value of 1.5 mm.

With decreasing angle α, the contribution of the adjacent part to the total field decreases. For very small poletips, the total field is predominantly determined by the adjacent part. For very wide poletips, the field is much less dependent on the adjacent part and thus on the angle α. As the angle α is already large in our case, the adjacent part can be considered as almost horizontal. The total outgoing flux is determined by the total area of poletip and adjacent part.

An entrance angle α is shown between a vertical axis and the incoming ray 54a, this angle is chosen sufficiently larger than the critical angle in order to fulfill the condition of total internal reflection. For a plastic to water interface this critical angle is typically 60 degrees.

The maximum thickness of the cartridge 30 is limited by the introduced spherical aberration that has to be corrected by the objective lens of the microscope 42. The maximum spherical aberration correction for commercial objective lenses accounts for 2 mm cover glass thickness. The minimum thickness of the cartridge is limited by mechanical strength and robustness, and is typical 0.3 mm.

The typical value of the sensor area of the sensor surface 31 to be imaged by the objective lens is determined by the minimum number of beads or particles 2 that has to be detected in order to obtain a sufficiently low Coefficient of Variation (CV). Since a single bead counting is accomplished by the first optical detection system 40, the CV is mainly governed by counting statistics and is given by:

$$CV = \frac{\sigma N}{N} = \frac{\sqrt{N}}{N} = \frac{1}{\sqrt{N}}$$

with N the number of bound beads or particles 2. The surface density of beads ñ is given by the volume density n times the channel height H: ñ=n·H. The total number of beads that can be detected, given a certain target concentration [T] (Mol/lit), and assuming that the bioassay has 100% efficiency, is therefore given by: N=[T]·103·NA·H·w2 where NA=6 1023 Mol-1 is the number of Avogadro. Since CV=1/√N, it follows that $$w = \frac{4.1}{\sqrt{CV^2 [T] H}}$$

with w, H in [mm], CV in [%] and [T] in [femtoMolar]. In order to achieve a CV of 10% or lower, the amount of beads within the field of view must at least be 100. To measure a target concentration of 1 fM with this accuracy, the width of the sensor area should be at least 0.6 mm.

The optical resolution is given by 0.5 λ/NA. A minimum value for the NA is required in order to resolve individual beads or particles 2. For a bead diameter of $d_{bead}$ the minimum value for the NA should be as $$NA_{min} = \frac{\frac{1}{2}\lambda}{d_{bead}}$$

For a bead diameter of 500 nm and a wavelength of 650 nm, the NA should be larger than 0.65 in order to optically resolve two adjacent beads or particles 2.

Because of aforementioned arguments the size of the gap 25 is more or less limited to a maximum value of 1.5 mm. The effective width wo of the sensor area of the sensor surface 31 that can be illuminated by the incoming ray 54a is determined by the thickness d of the cartridge 30, the entrance angle α, the required magnet air gap or gap 25 wm and the width of the pole tips t of the magnetic end sections 24a, 24b:

$$wo = 2d \cdot \tan \alpha - (wm + 2t)$$

For off-axis field coordinates (x>0) part of the cone 41 of light collected by the objective of the microscope 42 is obscured by the magnet pole tips of end sections 24a, 24b of the magnetic subunits 22a, 22b. As a result, the effective NA for this field coordinate x is reduced. In order to quantify this effect, the effective NA scales with the square root of the ratio of the obscured and unobscured areas of the light cones at the position of the magnet pole tips of the end sections 24a, 24b. From geometry considerations one can deduce:

$$\beta = \arctan(wm/2d)$$

$$\beta(x=0) = \beta$$

$$\beta(x=wm/2) = 0$$

$$\beta(x) = \arctan\left(\frac{wm/2 - x}{d}\right)$$

Note that x ranges from 0 to wo/2, and β(x) can be smaller than 0, i.e. more than half of the light cone 41 is being obscured, if wo>wm, or d·tan(α)>wm+t. The radius of the base of the cone 41 of light at the position of the magnet pole tips is given by:

$$r = d \cdot \tan \beta = wm/2, \text{ and}$$

$$r(x) = d \cdot \tan \beta(x) = wm/2 - x.$$

Next, we define these coordinates on a circle with unit radius: y(x)=r(x)/r=1−2x/wm. In this way x=0, y=1 means no obscuration, whereas for y=0 half of the light is being obscured by the pole tips. Now the base area A of that part of the cone that is being transmitted is given by the formula:

$$A(y) = \frac{1}{2} + \arcsin(y) + y\sqrt{1-y^2}.$$

Consequently, the effective NA at position x can be written as:

$$NA_{eff}(x) = n \cdot \sin\beta \cdot \sqrt{A(y(x))/A(y=0)} \sin\beta \cdot \sqrt{A(y(x))/\pi}$$

or:

$$NA_{eff}(x) = n \cdot \sin\beta \cdot \sqrt{\frac{1}{2} + \frac{1}{\pi} \cdot \arcsin(1 - 2x/wm) + \frac{1}{\pi} \cdot (1 - 2x/wm)\sqrt{1 - (1 - 2x/wm)^2}}$$

$$= n \cdot \sin(\arctan(wm/2d)) \cdot$$

$$\sqrt{\frac{1}{2} + \frac{1}{\pi} \cdot \arcsin(1 - 2x/wm) + \frac{1}{\pi} \cdot (1 - 2x/wm)\sqrt{1 - (1 - 2x/wm)^2}}$$

with x ranging from 0 to wo=2d·tan α−(wm+2t) and n the refractive index of the cartridge material.

From a biosensor point of view there are some restrictions with respect to the minimum required optical field wo, the minimum required numerical aperture NA and a maximum value for the magnet air gap wm. Relations found above now clearly define some design rules for the biosensor system 1.

Finally, the required values for our biosensor system 1 are a minimum NA of 0.4 over the full object field, a minimum object field of 1.0 mm, a maximum magnet air gap 25 of 1.5 mm.

Further, the required entrance angle α is α=65 degrees with d about 0.8 to 1.2 mm, α=70 degrees with d about 0.6 to 1.2 mm, α=75 degrees with d about 0.5 to 1.1 mm.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. A biosensor system for the detection of particles comprising:
   a biosensor cartridge including a sensor surface;
   a magnet assembly on one side of the cartridge configured to generate a magnetic field effective at the cartridge and the sensor surface, the magnet assembly including at least two magnetic subunits separated by a gap;
   a first optical detection system configured to detect the particles, the optical system being arranged at a same side of the cartridge as the magnet assembly;
   wherein the magnet assembly and the first optical detection system are configured such that:
   a light cone of an incoming ray generated by scattering at the particles projects through the gap between the at least two magnet subunits of the magnet assembly and the magnet assembly actuates the particles and the first optical detection system detects the particles at the sensor surface at the same time.

2. The biosensor system according to claim 1, comprising a second optical detection system configured to detect the particles, providing the light for the first optical detection system by scattering of light at the particles.

3. The biosensor system according to claim 2, wherein the second optical detection system is based on TIR (Total Internal Reflection) or on FTIR (Frustrated Total Internal Reflection) detection and the first optical detection system includes a microscope based on Dark Field Microscopy (DFM) configured to resolve single particles and a camera configured to image single particles resolved by the microscope.

4. The biosensor system according to claim 3, wherein the signals from the second optical detection system result from improper particles and the processor is further configured to subtract the signals from the second optical detector system from the signals from the first optical detection system such that the resulting signal characterizes only proper particles.

5. The biosensor system according to claim 1, wherein an entrance angle α between an incoming ray and outgoing ray of the first optical detection system lies in a range between 65° and 75°, the cartridge has a thickness d in a range between 0.3mm and 2mm, a width $w_{opt}$ of a sensor area of the sensor surface is about 1mm, numerical aperture (NA) of a lens has a minimum value satisfying the equation $$NA_{min} = \frac{\frac{1}{2}\lambda}{d_{bead}},$$

a width of a pole tip of the magnetic subunit is about 0.25mm, and the gap between the magnetic subunits is smaller than 1.5mm.

6. A method for the detection of particles with the biosensor system according to claim 1.

7. Use of a biosensor system according to claim 1 in one or more of the following applications:
   biosensors used for molecular diagnostics,
   rapid and sensitive detection of proteins and nucleic acids in complex biological mixtures such as e.g. blood or saliva,
   high throughput screening devices for chemistry, pharmaceuticals or molecular biology,
   testing devices e.g. for DNA or proteins e.g. in criminology, for on-site testing (in a hospital), for diagnostics in centralized laboratories or in scientific research,
   tools for DNA or protein diagnostics for cardiology, infectious disease and oncology, food, and environmental diagnostics,
   tools for combinatorial chemistry,
   analysis devices,
   nano- and micro-fluidic devices, and
   drug release and drug delivery systems (in particular transdermal and implantable drug delivery devices).

8. A biosensor system for detecting particles, comprising:
   a biosensor cartridge including a sensor surface;
   a magnet assembly on one side of the cartridge configured to generate a magnetic field effective at the cartridge and the sensor surface, the magnet assembly including at least two magnetic subunits separated by a gap;
   a first optical detection system configured to detect the particles through the gap between the magnet subunits, the first optical subsystem being arranged at a same side of the cartridge as the magnet assembly;
   a second optical detection system configured to detect the particles and provide light for the first optical detection system by scattering light at the particles; and
   wherein the magnet assembly is arranged essentially at a perpendicular direction relative to the second optical detection system, and the at least two subunits include end sections projecting essentially upwards in the same direction as the first optical detection system and perpendicular to the at least two subunits.

9. The biosensor system according to claim 8, further including:
   a processor configured to receive and process signals from the first optical detection system and the second optical detection system to generate a resulting signal characterizing a presence or location of at least one single particle.

* * * * *